United States Patent
Craig et al.

(10) Patent No.: US 8,933,051 B2
(45) Date of Patent: Jan. 13, 2015

(54) TREATMENT OF B-CELL LYMPHOMA WITH MICRORNA

(75) Inventors: Vanessa Craig, Zurich (CH); Anne Mueller, Dubendorf (CH)

(73) Assignee: University of Zurich, Zurich (CH)

( * ) Notice: Subject to any disclaimer, the term of this patent is extended or adjusted under 35 U.S.C. 154(b) by 0 days.

(21) Appl. No.: 13/876,725

(22) PCT Filed: Sep. 29, 2011

(86) PCT No.: PCT/EP2011/066980
§ 371 (c)(1),
(2), (4) Date: Mar. 28, 2013

(87) PCT Pub. No.: WO2012/041959
PCT Pub. Date: Apr. 5, 2012

(65) Prior Publication Data
US 2013/0195858 A1    Aug. 1, 2013

(30) Foreign Application Priority Data
Sep. 30, 2010    (EP) .................................... 10182950

(51) Int. Cl.
*A61K 48/00*    (2006.01)
*C07H 21/02*    (2006.01)
*C07H 21/04*    (2006.01)

(52) U.S. Cl.
USPC ............................ 514/44; 536/23.1; 536/24.5

(58) Field of Classification Search
CPC ........... C12Q 2600/178; C12Q 1/6886; C12Q 2600/112; C12N 15/113
See application file for complete search history.

(56) References Cited

U.S. PATENT DOCUMENTS

2006/0105360 A1 *    5/2006    Croce et al. ......................... 435/6
2009/0281298 A1 *    11/2009    Manoharan et al. .......... 536/24.5

FOREIGN PATENT DOCUMENTS

| WO | 2008/088858 A2 | 7/2008 |
| WO | 2008/092099 A2 | 7/2008 |
| WO | 2008/154333 A2 | 12/2008 |
| WO | 2009/108856 A2 | 9/2009 |

OTHER PUBLICATIONS

Craig et al., Myc-mediated repression of microRNA-34a promotes high-grade transformation of B-cell lymphoma by dysregulation of FoxP1. Blood. Jun. 9, 2011;117(23):6227-36. doi: 10.1182/blood-2010-10-312231. Epub Apr. 1, 2011.
International Search Report mailed Mar. 13, 2012 for Application No. PCT/EP2011/066980 (6 Pages).
Amini, et al., "A Novel B-cell Line (U-2932) Established from a Patient with Diffuse Large B-cell Lymphoma Following Hodgkin Lymphoma", Leukemia & Lymphoma, vol. 43 (11), pp. 2179-2189 (2002).
Hecht, et al., "Histiocytic Lymphoma Cell Lines: Immunologic and Cytogenetic Studies", Cancer Genetics and Cytogentics 14, 205-218 (1985).
Swerdlow, "Lymphoma classification and the tools of our trade: an introduction to the 2012 USCAP Long Course", Modern Pathology 26, S1-S4 (2013).
Chan, "Pathogenesis of diffuse large B cell lymphoma", International Journal of Hematology, Elsevier Science Publishers, NL, vol. 92, No. 2, Sep. 1, 2010, pp. 219-230.
Linnstaedt et al: "Virally Induced Cellular MicroRNA miR-155 Plays a Key Role in B-Cell Immortalization by Epstein-Barr Virus", Journal of Virology, val. 84, No. 22, Sep. 15, 2010, pp. 11670-11678.
Robertus et al: "Specific expression of miR-17-5p and miR-127 in testicular and central nervous system diffuse large B-cell lymphoma", Modern Pathology, vol. 22, No. 4, Mar. 13, 2009, pp. 547-555.

* cited by examiner

*Primary Examiner* — Amy Bowman
(74) *Attorney, Agent, or Firm* — Nutter McClennen & Fish LLP; Konstantin Linnik; Isaac A. Hubner (57) ABSTRACT

The invention relates to microRNA-34a and related microR-NAs for use in the treatment of B-cell lymphoma. Likewise it relates to microRNA-34a for use in the preparation of a medicament for the treatment of B-cell lymphoma, and for a method of treatment of B-cell lymphoma comprising administering microRNA-34a. These claims are based on the observation that microRNA-34a shows strong anti-proliferative effects when overexpressed in diffuse large B-cell lymphoma (gDLBCL) cell lines, or when delivered intratumorally or systemically in xenograft models of DLBCL.

19 Claims, 8 Drawing Sheets

B MALT-L     gDLBCL

TREATMENT OF B-CELL LYMPHOMA WITH MICRORNA

PRIORITY

This application claims the benefits of PCT application No. PCT/EP2011/066980, filed on Sep. 29, 2011, which claims priority of European Application No. 10182950.5 filed on Sep. 30, 2010; the content of both of these applications is incorporated by reference.

FIELD OF THE INVENTION

1. Sequence Listing

This application contains a sequence listing which is submitted under 37 CFR §1.821(c) in an electronic form as the text file P392A-ST25.txt, created on Mar. 21, 2013, the size of which is 1,595 bytes and the content of which is incorporated by reference.

The invention relates to the use of microRNA in the treatment of B-cell lymphoma.

2. Background of the Invention

Low-grade gastric mucosa-associated lymphoid tissue (MALT) lymphomas are extranodal B-cell lymphomas that arise in the context of chronic gastric inflammation induced by persistent *Helicobacter pylori* infection (Sagaert X. et al., Nat Rev Gastroenterol Hepatol 2010, 7(6):336-346). In its early stages, MALT lymphoma is an indolent and localized disease that can be treated by antibiotic eradication therapy targeting the underlying infection. In line with the concept that gastric MALT lymphomas are antigen-driven tumors, the surface immunoglobulins of MALT lymphoma B-cells are clonal, somatically hypermutated, and have undergone positive selection. MALT lymphoma tumor immunoglobulins (Igs) are polyreactive, i.e. they bind with similar affinity to various unrelated self and foreign antigens, and show a biased use of Ig $V_H$ gene segments previously linked to poly- and autoreactive antibodies (Craig V. J. et al., Blood 115:581-591 (2010)). Early MALT lymphomas further require T-cell help in the form of soluble T-helper cell-derived signals, most likely B-cell mitogenic cytokines such as IL-4 and IL-5.

Low grade MALT lymphomas may progress to more advance disease, either through the acquisition of one of three characteristic chromosomal translocations resulting in the constitutive activation of the NF-κB signaling pathway, or through the histologically evident transformation to high-grade gastric diffuse large B-cell lymphoma (gDLBCL). High grade transformation of *Helicobacter*-associated MALT lymphoma accounts for the majority of gDLBCL cases, whereas primary gDLBCL is rare. gDLBCL is characterized by antigen-independent growth, resistance to *Helicobacter* eradication therapy and a number of genetic alterations that may contribute to high grade transformation. In particular, TP53 mutations, Bcl6 overexpression and the aberrant DNA hypermethylation of tumor suppressor genes have been shown to be associated with high grade transformation. However, the precise molecular mechanisms underlying the transition from low-grade MALT lymphoma to gDLBCL remain largely unclear. MicroRNAs (miRNAs) are an abundant class of small non-coding RNAs, which modulate the expression of their target genes at the post-transcriptional level. Aberrant expression of specific miRNAs has been associated with both solid and hematopoietic malignancies, including chronic lymphocytic leukemia, lung cancer and ovarian cancer. The majority of human miRNAs are located at fragile sites or cancer associated genomic regions. For example, the frequent down-regulation of the fragile region encoding miR-15a (microRNA-15a) and miR-16-1 promotes CLL through dysregulation of the Bcl2 oncogene. The widespread deregulation of the miRNA transcriptome appears to be a hallmark of cancer and has been attributed to deletions, amplifications or mutations of miRNA loci, epigenetic silencing or aberrant transcriptional regulation of miRNA genes. Many studies have revealed the potential of miRNA expression profiles as diagnostic and prognostic markers of cancers, which may be more useful than expression analysis of protein-coding genes for the classification and stratification of cancer subtypes (Zhang B. et al., Dev Biol 2007, 302(1):1-12).

MicroRNA profiling in Burkitt lymphoma demonstrated a very characteristic MYC induced microRNA expression. This indicates that MYC regulates Burkitt lymphoma cell fate in a direct mode at the transcription level and indirectly at the translational level (Robertus J. L. et al., Brit J Haematol 2010, 149:896-899). In chronic lymphocytic leukemia (CLL) patients with TP53 abnormalities exhibit downregulation of miR-34a, miR-29c and mirR-17-5p (Mraz M. et al., Leukemia 2009, 23:1159-63).

SUMMARY OF THE INVENTION

The invention relates to microRNA, such as microRNA-34a, for use in the treatment of B-cell lymphoma, in particular gastric B-cell lymphoma, non-gastric diffuse large B-cell lymphoma, extranodal diffuse large B-cell lymphoma, Burkitt lymphoma and chronic lymphocytic leukemia. Likewise it relates to microRNA, such as microRNA-34a, for use in the preparation of a medicament for the treatment of B-cell lymphoma, and for a method of treatment of B-cell lymphoma comprising administering microRNA, such as microRNA-34a.

BRIEF DESCRIPTION OF THE FIGURES

Quantification of let-7a (A) and miR-34a (B) expression in gastritis (G), low grade MALT lymphoma (MALT-L) and gastric diffuse large B-cell lymphoma (gDLBCL) samples by LNA real-time RT-PCR; absolute expression was normalized to U6 snRNA. ns: not significant.

(A, B) Myc expression was analyzed by immunohistochemistry on a tissue microarray comprising 37 gDLBCL and 39 low grade MALT lymphoma (MALT-L) cases. The fraction of MALT lymphoma and gDLBCL cases with high (black), low (grey) and no Myc expression (white) is indicated in A; representative micrographs are shown in B. The scale bar indicates 50 µm.

(C, D) Quantification of let-7a (C) and miR-34a (D) expression as determined by LNA real-time RT-PCR for the cells lines U2932 (white) and SUDHL4 (black) 48 h after electroporation with Myc-specific (MYC) or scrambled (C=control) siRNA. Expression values were normalized to U6 snRNA levels.

(E, F) Proliferation as assessed by [$^3$H] thymidine incorporation of U2932 (E) and SUDHL4 (F) cells 72 h after electroporation with Myc-specific or scrambled (C=control) siRNA.

(G, H) U2932 (G) and SUDHL4 (H) cells were electroporated with the indicated pre-miRs or scrambled negative control (C) oligonucleotide 72 h prior to the quantification of proliferation by [$^3$H] thymidine incorporation.

(A) U2932 cells were electro-porated with pre-miR34a or a scrambled negative control (C) pre-miR and analyzed with respect to FOXP1 expression 48 h later. FOXP1 transcript levels were normalized to GAPDH expression.

(B) FoxP1 protein levels of the experiment described in A as analyzed by Western blot. α-Tubulin (α-T) levels are shown to control for equal loading.

(C) Dual luciferase assay of HEK293T cells co-transfected with firefly luciferase constructs containing the wild-type (WT) or mutant (M) miR-34a target site of the FOXP1 3'-UTR region downstream of the luciferase reporter. Cells were co-transfected with either pre-miR-34a or a negative control (C) scrambled oligonucleotide and the respective luciferase construct. Data are represented as relative luciferase activity (Luc).

(A, B) FoxP1 expression was analyzed by immunohistochemistry on the tissue microarray described in FIG. 2. The fraction of MALT lymphoma (MALT-L) and gDLBCL cases with high (black), low (grey) and no Myc expression (white) is indicated in A; representative micrographs are shown in B. The scale bar indicates 50 μm.

(C-F) U2932 (C), SUDHL4 (D), SUDHL6 (E) and SUDHL7 (F) cells were electroporated with pre-miR34a, a FoxP1-specific siRNA or the respective negative control (C) scrambled oligonucleotides 72 h prior to the quantification of proliferation by [$^3$H] thymidine incorporation.

Local treatment with mir-34a inhibits the growth of DLBCL xenografts. NOD/SCID mice were inoculated subcutaneously in both flanks with 1×10$^7$ U2932 cells. Palpable tumors were locally injected every 3 days either with 12.5 μg miR-34a (n=10) or 12.5 μg scrambled negative control (NC) miRNA (n=12) for a period of 15 days.

(A) Tumor volume (mm$^3$) was calculated via caliper measurements every 3 days using the formula: (a$^2$×b)/2, where a is the shorter and b the longer dimension of the tumor. Tumor volume (mm$^3$) is shown as function of days of treatment with either miR-34a or negative control (NC). Bars represent SEM. P values were obtained using Student's t test: ***, P<0.001.

(B) Scatter plot showing the final tumor weights (gr) of the NC and miR-34a-treated xenografts.

(C) Quantitative real time PCR analysis of miR-34a levels in tumors treated with either miR-34a or NC miRNA. Expression values were normalized against the U6 snRNA. P values were obtained using Student's t test: *, P<0.05; ***, P<0.001. Data represent 3 independent experiments.

Systemic delivery of mir-34a blocks tumor growth. 1×10$^7$ U2932 cells were inoculated subcutaneously in both flanks of NOD/SCID mice. Once tumors reached a palpable volume the mice were intravenously injected with 20 μg of formulated miR-34a (n=7) or PBS (negative control, NC) (n=7) every 2 days. The final injection was performed on day 13, 10 minutes before the study endpoint.

(A) Tumor volumes (mm$^3$, determined as explained for FIG. 5(A)) were measured every 2 days. Bars represent SEM. P values were obtained using Student's t test: *, P<0.05; , P<0.01, *, P<0.001.

(B) Tumor weights (gr) of the NC and miR-34a-treated xenografts.

(C) miR-34a levels were measured by quantitative real time PCR in tumors treated with either miR-34a or NC miRNA. Expression values were normalized against the U6 snRNA. Data represent 2 independent experiments.

DETAILED DESCRIPTION OF THE INVENTION

Real time RT-PCR revealed the microRNA miR-34a to be differentially regulated in gastric low grade MALT lymphoma and its transformed high grade disease counterpart, gastric diffuse large B-cell lymphoma (gDLBCL). miR-34a is negatively regulated by Myc, an oncogene overexpressed in gDLBCL. Bioinformatic target prediction combined with functional analyses revealed that miR-34a represents a tumor suppressor miRNA in gDLBCL, which acts through post-transcriptional control of its direct target FoxP1, a hematopoietic oncoprotein overexpressed in gDLBCL. These findings identify a new mechanism that links the aberrant expression of Myc and the resulting repression of the tumor suppressor miRNA miR-34a to FoxP1 deregulation in high grade transformation of gastric B-cell lymphoma.

Related observations have been made in Burkitt lymphoma and in chronic lymphocytic leukemia, two non-gastric mature B-cell neoplasms.

The invention relates to microRNA, such as microRNA-34a, for use in the treatment of B-cell lymphoma, in particular gastric B-cell lymphoma, non-gastric diffuse large B-cell lymphoma, extranodal diffuse large B-cell lymphoma, Burkitt lymphoma and chronic lymphocytic leukemia.

MicroRNAs (miRNAs) are short ribonucleic acid (RNA) molecules 13 to 25 nucleotides long. MicroRNAs are post-transcriptional regulators that bind to complementary sequences in the 3' untranslated regions (3' UTRs) of target messenger RNA transcripts usually resulting in gene silencing. MicroRNA-34a (miR-34a) is a member of the miR-34 family, which is composed of miR-34a, miR-34b, miR-34c-5p and miR-34c-3p. The miR-34a gene is located on chromosome 1p36.22. MicroRNAs considered in the present invention are miR-34a, miR-34b, miR-34c-5p, miR-34c-3p, miR-15a, miR-23a, miR-26a, miR-150, and let-7a.

```
MicroRNA-34a has the sequence
                               (SEQ ID NO: 1)
UGGCAGUGUCUUAGCUGGUUGU.

MicroRNA-34b has the sequence
                               (SEQ ID NO: 2)
CAAUCACUAACUCCACUGCCAU.

MicroRNA-34c-5p has the sequence
                               (SEQ ID NO: 3)
AGGCAGUGUAGUUAGCUGAUUGC.

MicroRNA-34c-3p has the sequence
                               (SEQ ID NO: 4)
AAUCACUAACCACACGGCCAGG.

MicroRNA-15a has the sequence
                               (SEQ ID NO: 5)
UAGCAGCACAUAAUGGUUUGUG.

MicroRNA-23a has the sequence
                               (SEQ ID NO: 6)
AUCACAUUGCCAGGGAUUUCC.

MicroRNA-26a has the sequence
                               (SEQ ID NO: 7)
UUCAAGUAAUCCAGGAUAGGCU.
```

-continued

```
MicroRNA-150 has the sequence
                              (SEQ ID NO: 8)
UCUCCCAACCCUUGUACCAGUG.

MicroRNA let-7a has the sequence
                              (SEQ ID NO: 9)
UGAGGUAGUAGGUUGUAUAGUU.
```

Gastric B-cell lymphoma is a non-Hodgkin's lymphoma of the stomach. In particular, gastric B-cell lymphoma is high-grade gastric diffuse large B-cell lymphoma (gDLBCL). Burkitt lymphoma is a further B-cell non-Hodgkin lymphoma. Chronic lymphocytic leukemia (CLL) is the most common leukemia, and also represents a B-cell lymphoma. The invention can also be applied to non-gastric diffuse large B-cell lymphoma and extranodal diffuse large B-cell lymphoma.

The invention further relates to microRNA, such as microRNA-34a, for use in the preparation of a medicament for the treatment of B-cell lymphoma, in particular gastric B-cell lymphoma, non-gastric diffuse large B-cell lymphoma, extranodal diffuse large B-cell lymphoma, Burkitt lymphoma and chronic lymphocytic leukemia.

For the administration, the active ingredient is preferably in the form of a pharmaceutical preparation comprising a microRNA as active ingredient in chemically pure form or suitably derivatized, and optionally a pharmaceutically acceptable carrier and optionally adjuvants.

The microRNA is used in an amount effective against the disease in humans. The dosage of the active ingredient depends upon the age, weight, and individual condition of the human being, the individual pharmacokinetic data, and the mode of administration. In the case of an individual human having a bodyweight of about 70 kg the daily dose administered of a microRNA is from 0.01 mg/kg bodyweight to 100 mg/kg bodyweight, preferably from 0.1 mg/kg bodyweight to 50 mg/kg bodyweight, more preferably from 1 mg/kg to 20 mg/kg bodyweight administered as a single dose or as several doses. The microRNA can be used alone or in combinations with other drugs.

MicroRNAs of the invention are applied in unmodified form, preferably as duplexes involving complementary RNA (double-stranded RNA), chemically modified in part as 2'-O-methylpurines or 2'-fluoropyrimidines, or as asymmetrical Dicer substrates with a blunt end which includes two DNA bases and a two nucleotide overhang at the 3' end. Dicer is an endoribonulclease of the RNases III family that cleaves double-stranded RNA into short double stranded RNA fragments and catalyzes formation of the RNA-induced silencing complex. Another envisaged derivative of microRNA is double-stranded RNA chemically bound at the 3' hydroxy group to cholesterol. Further derivatives considered are those indicated in Kim D. H. and Rossi J. J., Nature Reviews Genetics, 2007, 8:173-184.

Pharmaceutical compositions for parenteral administration, such as subcutaneous, intravenous, intrahepatic or intramuscular administration, are especially preferred. The pharmaceutical compositions comprise from approximately 1% to approximately 95% active ingredient, preferably from approximately 20% to approximately 90% active ingredient.

For parenteral administration preference is given to the use of solutions of the microRNA and microRNA derivatives, and also suspensions or dispersions, especially isotonic aqueous solutions, dispersions or suspensions which, for example, can be made up shortly before use. The pharmaceutical compositions may be sterilized and/or may comprise excipients, for example preservatives, stabilizers, wetting agents and/or emulsifiers, solubilizers, viscosity-increasing agents, salts for regulating osmotic pressure and/or buffers and are prepared in a manner known per se, for example by means of conventional dissolving and lyophilizing processes.

In particular, formulations for parenteral administration may contain, for example, excipients, sterile water or saline, polyalkylene glycols such as polyethylene glycol, oils of vegetable origin, biodegradable lactide polymers, lactide/glycolide copolymers, polyoxyethlene-polyoxypropylene copolymers, ethylene-vinyl acetate copolymers, cyclodextrins, porphyrin derivatives, polyethylenimine polymers, lipofectin, atelocollagen, polylysine, nanoparticles, microspheres and liposomes, in particular liposomes formed from phospholipid bilayers.

Liposomes suitable in the invention are formed from standard vesicle-forming lipids, which generally include neutral or negatively charged phospholipids and a sterol, such as cholesterol. The selection of lipids is generally guided by consideration of factors such as desired liposome size and half-life of liposome in the blood stream. Further considered are liposomes modified so as to avoid clearance by the mononuclear macrophages and reticuloendothelial systems, for example having opsonization-inhibition moieties bound to the surface of the liposome structures. Opsonization-inhibition moieties are large hydrophilic polymers bound to the liposome membrane, for example polyethylene glycol or polypropylene glycol and derivatives thereof, e.g., methoxy derivatives or stearates, or also synthetic polymers such as polyacrylamide or polyvinyl-pyrrolidone, linear, branched or dendrimeric polyamidoamines, polyacrylic acids, polyalcohols, e.g. polyvinyl alcohols and polyxylitol, and gangliosides. Preferred opsonization-inhibition moieties are polyethylene glycol or polypropylene glycol and derivatives thereof giving rise to "pegylated liposomes", resulting in stable nucleic acid-lipid particles (SNALPs, Kim D. H. and Rossi J. J., Nature Reviews Genetics, 2007, 8:173-184).

Further considered are pharmaceutical compositions for selective systemic delivery, for example coupled to antibody fragments, aptamers or packaged into nanoparticles coated with receptor-targeting ligands.

The microRNA can be administered alone or in combination with one or more other therapeutic agents, possible combination therapy taking the form of fixed combinations of the microRNA and one or more other therapeutic agents known in the treatment of gastric B-cell lymphoma in humans, the administration being staggered or given independently of one another, or being in the form of a fixed combination.

Possible combination partners considered are cyclophosphamide, hydroxydaunorubicin (doxorubicin, adriamycin), oncovin (vincristine), prednisone/prednisolone, and rituximab.

Pharmaceutical preparations according to the invention are manufactured by methods known in the art, especially by conventional mixing, coating, granulating, dissolving or lyophilizing.

The invention further relates to a method of treatment of B-cell lymphoma, in particular gastric B-cell lymphoma, non-gastric diffuse large B-cell lymphoma, extranodal diffuse large B-cell lymphoma, Burkitt lymphoma and chronic lymphocytic leukemia, comprising administering to a patient in need thereof a therapeutically effective amount of a microRNA, such as microRNA-34a.

Figure 1:
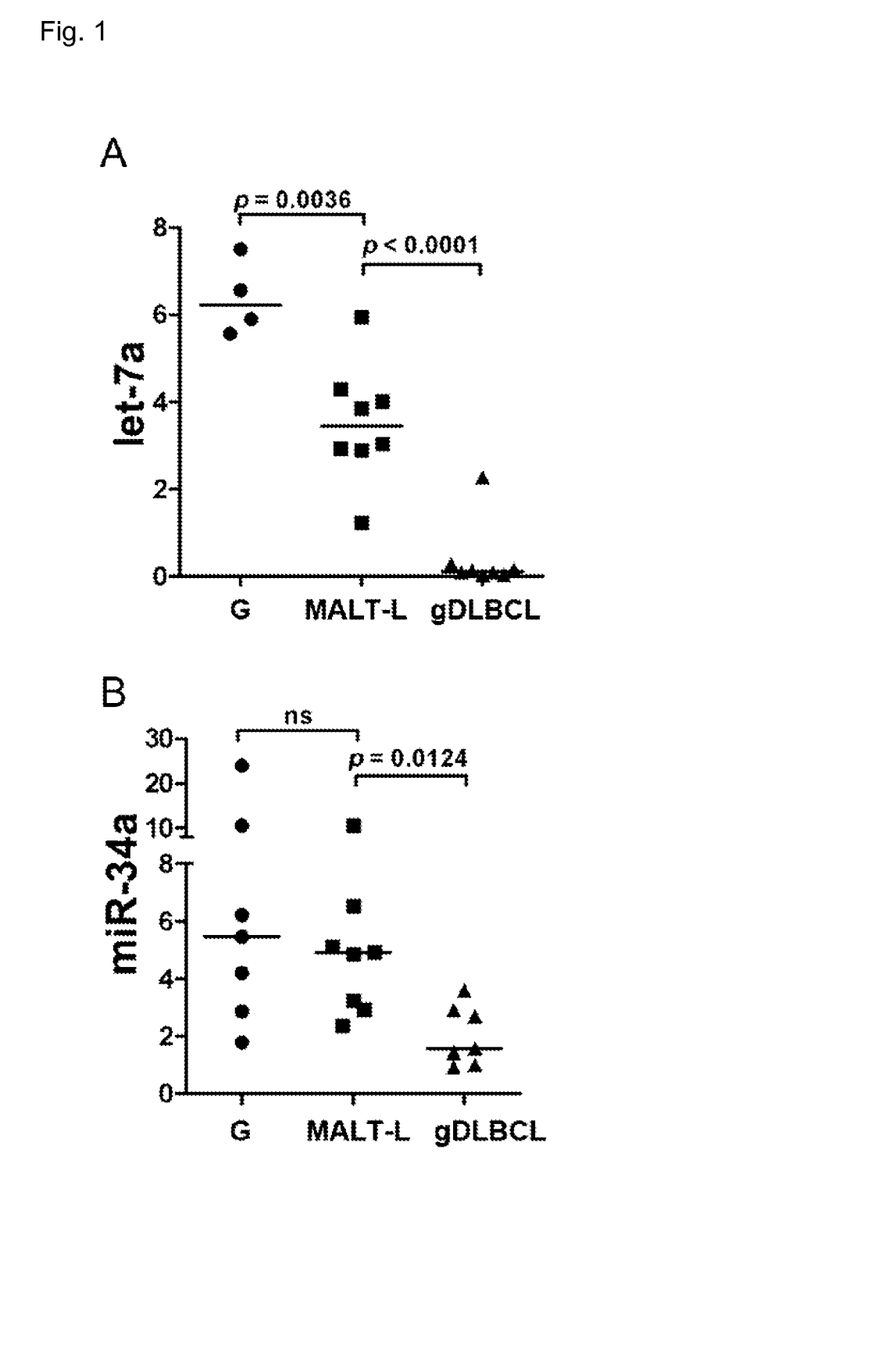
FIG. 1. MicroRNA expression levels of miR-34a and let-7a in gastritis, low grade MALT lymphoma and gDLBCL.

The scientific rationale for the use of a microRNA, such as microRNA-34a, in the treatment of gastric B-cell lymphoma and related B-cell lymphoma is as follows:

miR-34a is Specifically Down-Regulated in High Grade-Transformed Gastric Lymphoma Total RNA isolated from 7-8 cases each of *Helicobacter*-associated reactive gastritis, low grade MALT lymphoma and high grade gDLBCL was subjected to real time RT-PCR in order to determine the differential expression patterns of two selected miRNAs, let-7 and miR-34a (FIG. 1A, B). In conclusion, it was found that high grade transformation of gastric MALT lymphoma is accompanied by down-regulation of miR-34a.

Figure 2:
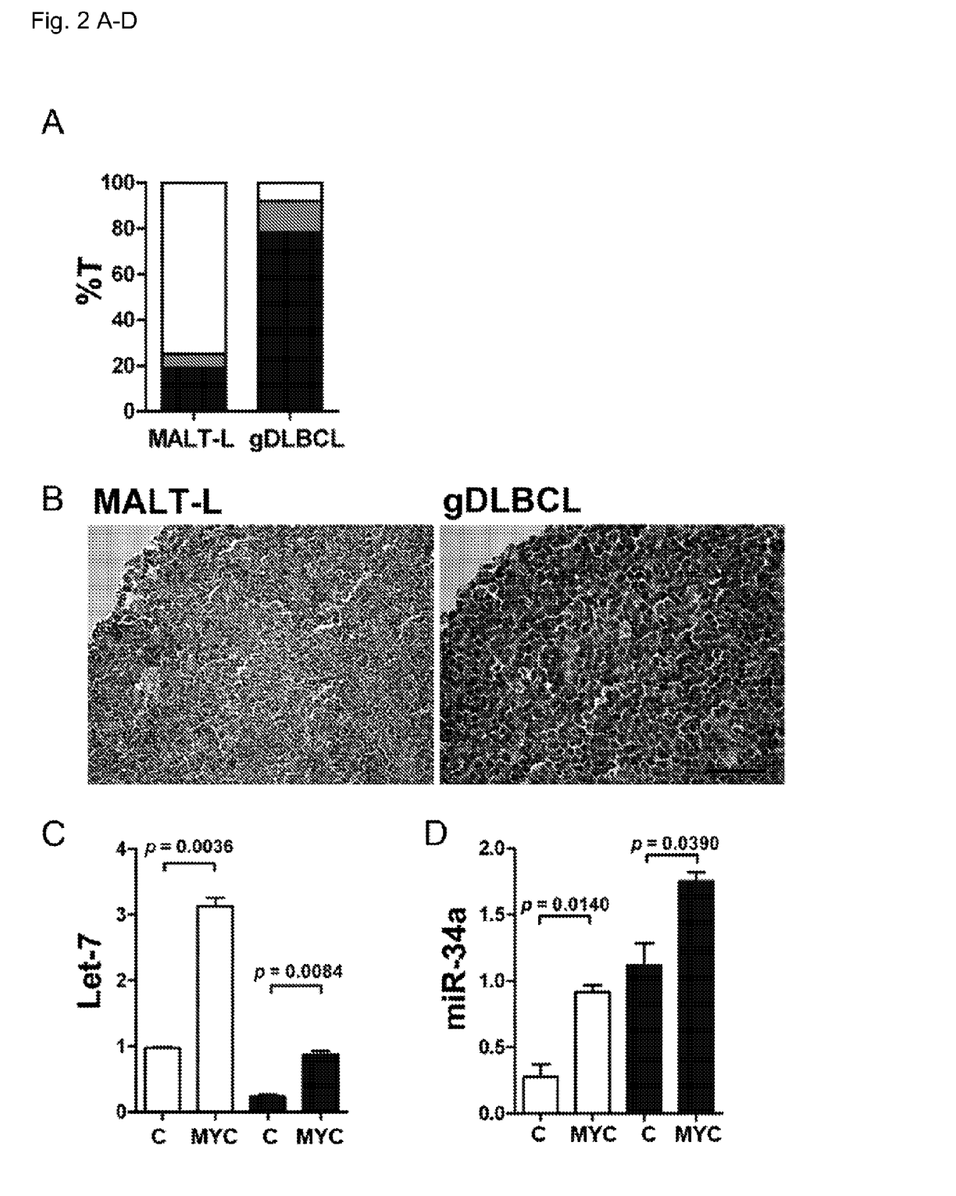
FIG. 2. Myc is over-expressed in gastric diffuse large B-cell lymphoma (gDLBCL) and exhibits oncogenic properties in DLBCL cell lines in vitro.

Myc is Over-Expressed in High Grade Gastric DLBCL and Controls DLBCL Proliferation In Vitro Since Myc is known to negatively regulate miR-34a expression, the Myc expression status of a set of 37 gDLBCL and 39 low grade MALT lymphomas spotted onto a gastric lymphoma tissue microarray was assessed. Indeed, 80% of gDLBCL, but only 20% of low grade lymphomas showed high expression of Myc (FIG. 2A, B), indicating that Myc expression may be a useful marker for the differential diagnosis of both disease entities. To assess a possible causal link between Myc expression and miRNA down-regulation in DLBCL, Myc expression was transiently knocked down in two DLBCL lines, of which one had the characteristics of the 'activated B-cell' type of DLBCL ('ABC'; U2932) and the other had typical 'germinal center' type features ('GC', SUDHL4). The transient knock-down of Myc indeed increased expression of both let-7 (FIG. 2C) and miR-34a (FIG. 2D) in both cell lines in relation to a scrambled siRNA. Interestingly, the proliferation of both cell lines as determined by [$^3$H] thymidine incorporation was significantly reduced upon siRNA-mediated Myc knock down (FIG. 2E, F), indicating that Myc expression drives lymphoma cell proliferation, possibly via down-regulation of tumor suppressive miR-NAs.

To determine which of the Myc-repressed miRNAs have tumor suppressive properties in DLBCL cell lines in vitro, a panel of six miRNAs that were consistently predicted by both the TargetScan and PicTar algorithms to target known or putative hematopoietic oncogenes such as Bcl6, Ezh2, FoxP1 and Pax5 were analyzed. Synthetic, chemically modified double-stranded precursor molecules of the six miRNAs (so-called pre-miRs™) were introduced into U2932 and SUDHL4 cells by nucleoporation using the Amaxa system, either alone or in combination (FIG. 2G, H). While all miRNAs on this panel had suppressive effects on tumor cell proliferation in relation to an unspecific negative control miRNA, one candidate, miR-34a, was particularly effective in this respect (FIG. 2G, H). miR-34a is a known tumor suppressor miRNA in prostate and lung cancer and is a lead candidate for miRNA replacement therapy for the treatment of these malignancies (Wiggins J. F. et al., Cancer Res 2010, 70:5923-30). This combined bioinformatic and experimental approach identified a miRNA with interesting tumor suppressive characteristics in DLBCL in vitro.

miR-34a Targets the Transcription Factor FoxP1 in DLBCL

Figure 3:
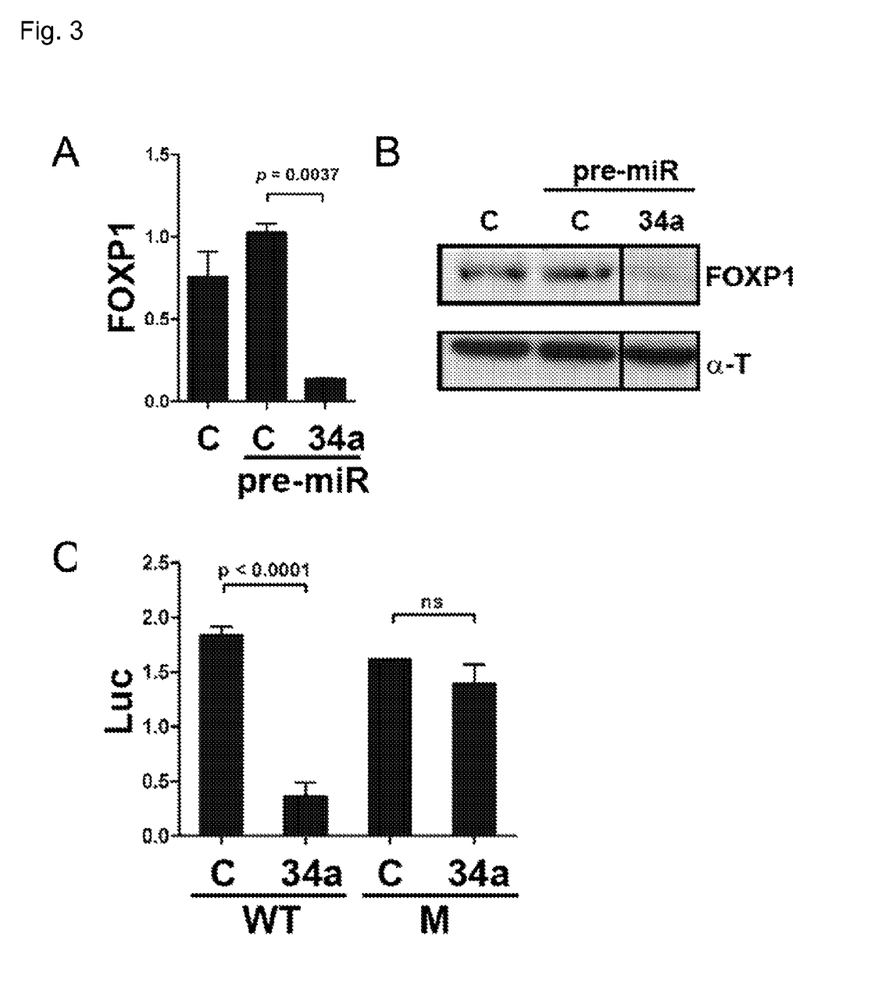
FIG. 3. MiR-34a directly targets FOXP1 in DLBCL.

Bioinformatically predicted targets of miR-34a include the transcription factors Bcl6 and FoxP1, which harbor one and two putative miR-34a seed regions in their 3' untranslated region (UTR), respectively. As both have previously been linked to the pathogenesis of gDLBCL, their possible post-transcriptional regulation by miR-34a was tested in the DLBCL cell lines introduced earlier. Quantitative RT-PCR of FoxP1 and Bcl6 expression after nucleoporation of U2932 and SUDHL4 cells with pre-miR-34a revealed that FoxP1, but not Bcl6, is a likely direct target of this miRNA (FIG. 3A). Protein levels of FoxP1 were also strongly reduced upon introduction of miR-34a into U2932 cells (FIG. 3B). In order to measure a direct effect of miR-34a binding to its seed regions in the foxp1 gene, the wild type sequence of the seed region, or a mutant version in which four of the six positions had been mutated, was cloned downstream of a luciferase reporter gene. Co-transfection of pre-miR-34a with the luciferase expression vector harboring the wild type seed region, but not the mutant version, blocked reporter gene expression as assessed by luciferase activity assay (FIG. 3C). The results demonstrate that FoxP1, but not Bcl6, is a target of miR-34a in DLBCL cell lines.

The miR-34a Target FoxP1 is a Bona Fide Oncoprotein in DLBCL

Figure 4:
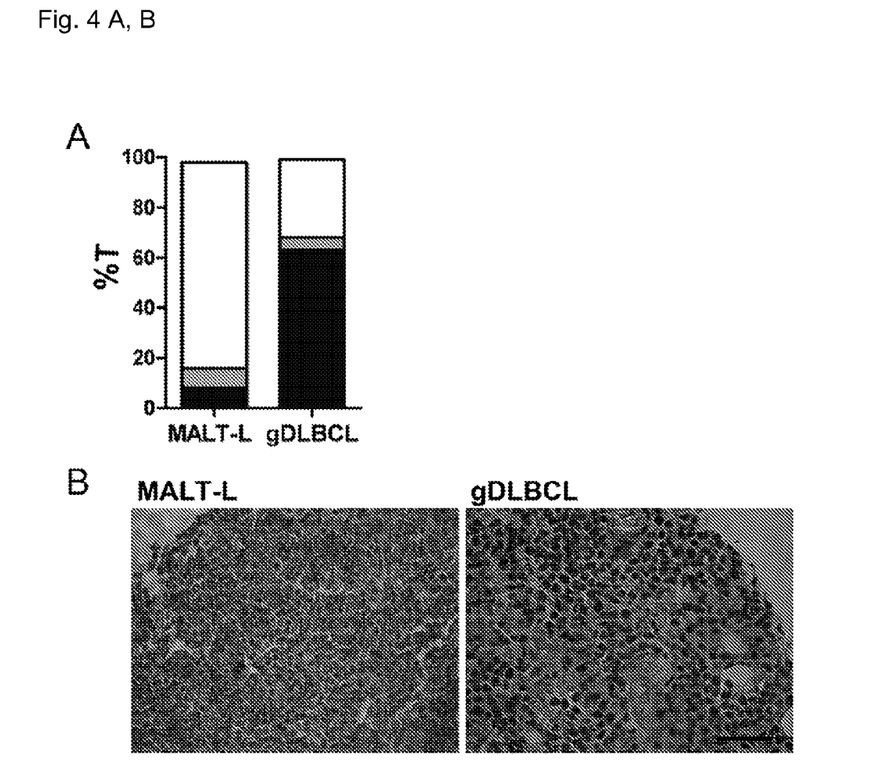
FIG. 4. FOXP1 is a bona fide oncoprotein in DLBCL.

As FoxP1 is a direct target of miR-34a, and an indirect target of Myc, it was tested whether FoxP1 is differentially expressed in gDLBCL and low grade MALT lymphoma. Indeed, a majority of gDLBCL, but very few of the low grade lymphoma cases spotted onto the tissue microarray showed reactivity with a FoxP1-specific antibody (FIG. 4A, B). Interestingly, all FoxP1-positive cases also expressed Myc, irrespective of whether they were classified as low grade or high grade lymphomas. On the other hand, FoxP1 expression did not overlap with expression of Bcl6, which is often used to distinguish between 'GC' and 'ABC' type DLBCL: similar proportions of FoxP1-positive cases were Bcl6-positive and -negative. An siRNA-mediated knock down of FoxP1 should have similar anti-proliferative effects in DLBCL cell lines as the delivery of miR-34a. This was indeed the case: knock down of FoxP1 blocked the proliferation of four 'GC' and 'ABC' type DLBCL cell lines at similar levels, and roughly as efficiently as the re-introduction of miR-34a (FIG. 4C-F). In conclusion, the results suggest that the transcription factor FoxP1 is a direct target of miR-34a in gDLBCL and is overexpressed in a majority of gDLBCL, but not in low grade lymphoma cases, and represents a bona fide oncoprotein in this disease entity.

Figure 5:
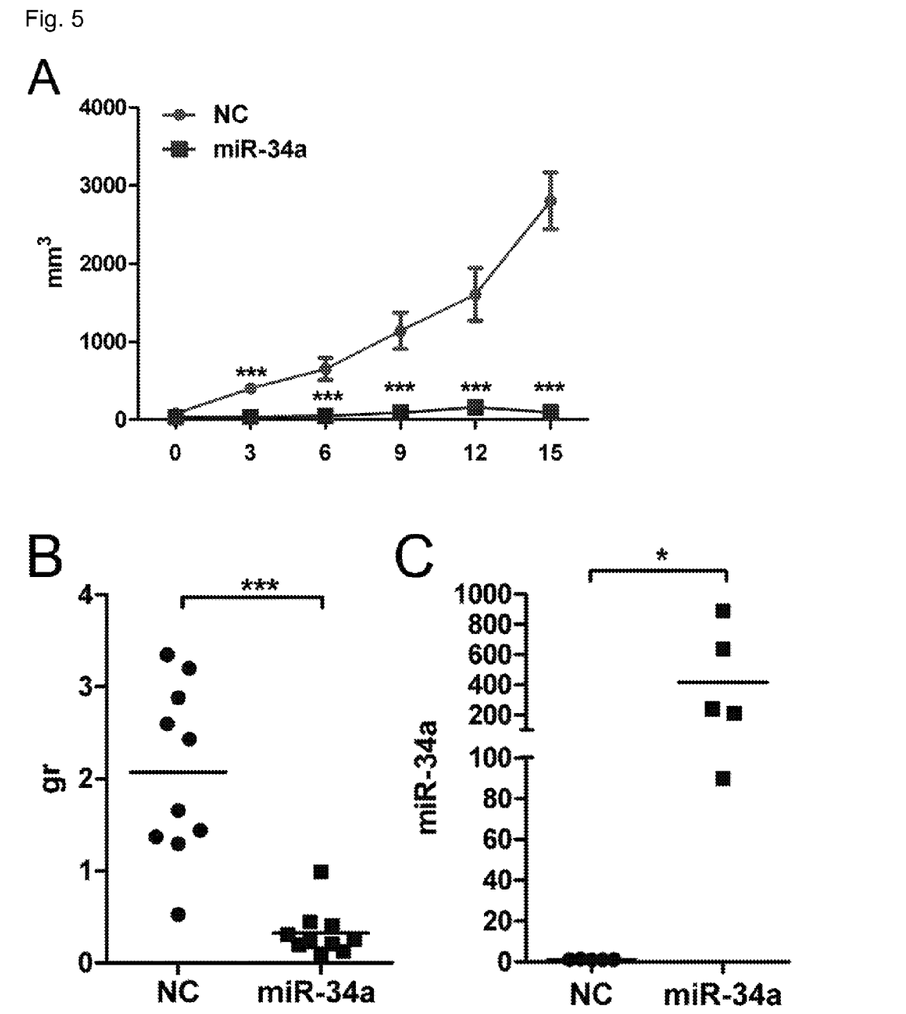
FIG. 5. Intratumoral delivery of formulated miR-34a blocks DLBCL growth in vivo.

Intratumoral Delivery of microRNA-34a Abrogates Growth of Diffuse Large B-Cell Lymphoma In Vivo Based on a previous study (Wiggins J. F. et al., Cancer Res 2010, 70:5923-30) documenting the efficacy of miRNA replacement in preventing tumor growth in mouse models of non-small-cell lung cancer, a possible therapeutic effect of intratumorally administered miR-34a was examined in a xenograft model of DLBCL. Severely immunocompromised NOD/SCID/IL2Rg$^{-/-}$ mice lacking B-, T- and NK cells were inoculated subcutaneously with U2932 cells, an ABC type DLBCL cell line with no or very little miR-34a expression due to promoter hypermethylation. Once palpable tumors of ~50 mm$^2$ had formed, the mice received regular intratumoral doses of miR-34a or negative control miRNA formulated in lipid-based transfection reagent at three-day intervals for 15 days. Whereas the tumors in the negative control group grew rapidly in this time frame, a strong reduction of tumor growth was observed in the miR-34a-treated group (FIG. 5A). The difference in tumor volume between the treatment groups was evident macroscopically, and was reflected in significantly different tumor weights at the study endpoint (FIG. 5B). Whereas miR-34a expression was hardly detectable in the tumors of the negative control group, its levels were strongly increased in the miR-34a-treated group (FIG. 5C). The difference in miR-34a expression was not due to miRNA accumulating in the interstitial space, but rather reflected its uptake into the tumor cells as assessed in single cell suspensions after 24 hours of culturing ex vivo.

Figure 6:
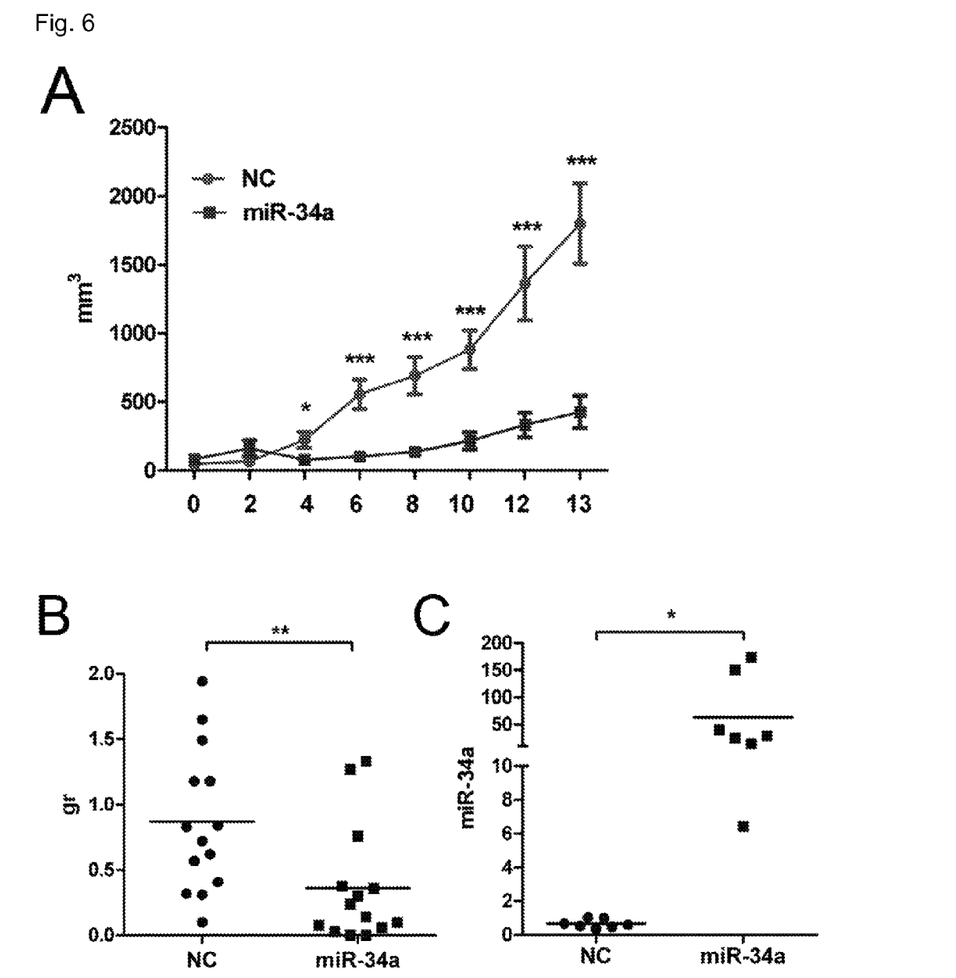
FIG. 6. Systemic treatment with formulated miR-34a suppresses growth of DLBCL in vivo.

Systemic Delivery of microRNA-34a Abrogates Growth of Diffuse Large B-Cell Lymphoma In Vivo Based on the promising results of the intratumoral treatments, a strategy to systemically deliver miR-34a or control miRNA was devised in the U2932 xenograft model. Synthetic miR-34a mimic or control miRNA was formulated in neutral lipid emulsion and the therapeutic benefit of regular intravenous injections examined in the U2932 model. NOD/SCID/IL2Rg$^{-/-}$ mice subcutaneously implanted with U2932 cells were started on the treatment once their tumors had reached a size of ~50 mm$^2$; each mouse received a total of eight doses and was monitored closely with respect to its tumor volume and possible side effects for the duration of the treatment. None of the treated mice exhibited adverse symptoms in the course of the treatment, nor did any of the mice included in the study develop abnormalities that would have been evident at necropsy. As with the intratumoral treatment, a strong reduction in tumor growth was observed in mice receiving NLE-formulated miR-34a mimic compared to mice in the negative control group (FIG. 6A). The differences in tumor volume between the treatment groups were again reflected in significantly different tumor weights at the study endpoint (FIG. 6B). The tumors of miR-34a-treated mice exhibited substantially higher levels of miR-34a than control tumors (FIG. 6C); other organs such as the liver and spleen also differed between the treatment groups in terms of miR-34a expression levels, but not to the same extent as the tumors themselves. This result can probably be attributed to the fact that the nucleotide sequence of mature miR-34a of mice and humans is identical, and that the quantitative PCR therefore cannot differentiate between the endogenously expressed miRNA and the ectopically delivered mimic. As the miR-34a baseline expression is higher in liver tissue than in the xenograft tumors, its accumulation upon systemic administration is more evident in the tumors. In conclusion, systemic delivery of miR-34a to xenograft DLBCL tumors is feasible and efficiently prevents tumor growth without producing adverse side effects; the results imply that miRNA replacement is suitable for the treatment of DLBCL patients with transcriptional or epigenetic silencing of this and related tumor suppressor miRNA.

The results taken together establish a mechanistic link between overexpression of Myc, the concomitant repression of Myc-regulated miRNA genes, and the deregulation of FoxP1. Chromosomal translocations involving the MYC locus are reported in the literature for 50-60% of gDLBCL, but are never detected in gastric low grade lymphomas and rarely found in nodal DLBCL. While chromosomal translocations involving the MYC locus are the likely cause for Myc overexpression in gDLBCL, other alternative mechanisms of Myc deregulation are conceivable. Myc is known to be post-transcriptionally regulated by miRNAs. Interestingly, several Myc-regulating miRNAs (including miR-34a and let7) are also targets of Myc repression, establishing a feedback loop that aggravates and perpetuates the effects of Myc overexpression and may thus contribute to cancer progression. Several lines of evidence argue that miR-34a is a strong tumor suppressor miRNA in solid cancers. It is located on chromosome 1p36.22 in a region that has previously been associated with various malignancies, including lung cancer; it is transcriptionally induced by the tumor suppressor p53 and its overexpression inhibits growth of various cancer types in vitro. The first proof of principle for the success of miR-34a "replacement therapy" in cancer treatment was recently reported using a preclinical model of non-small cell lung cancer; the local and systemic delivery of chemically synthesized miR-34a was achieved in this model by formulation with a lipid-based delivery reagent (Wiggins J. F. et al., Cancer Res 2010, 70:5923-30).

It is demonstrated here for the first time that miR-34a has tumor suppressive properties in a hematopoietic malignancy. It is down-regulated in the malignant compared to the benign form of gastric lymphoma and its expression is directly regulated by Myc, which is shown to possess oncogenic properties in various DLBCL cell lines. Ectopic miR-34a re-expression prevents DLBCL growth in vitro; its intratumoral or systemic delivery prevents tumor growth in a xenograft model. Finally, it is demonstrated that miR-34a targets a suspected hematopoietic oncogene in gastric lymphoma, FoxP1, which is overexpressed in the malignant form of gastric lymphoma and which possesses bona fide oncogenic properties in DLBCL. The post-transcriptional regulation of FoxP1 by miR-34a further provides a plausible explanation for the conundrum that FoxP1 is highly expressed in many lymphomas not harboring the rare chromosomal translocation t(3; 14)(p13; q32), which juxtaposes the FOXP1 and IGH gene loci in certain non-gastric MALT lymphomas and extranodal DLBCL.

MiR-34 replacement therapy should therefore be considered for the treatment of patients with miR-34a-negative, FoxP1-overexpressing hematopoietic malignancies such as gastric DLBCL. The beneficial therapeutic effects of miR-34a are due to the strong tumor suppressive properties of this miRNA, which are exerted via its oncogene target FoxP1.

Patient Material and DLBCL Cell Lines

For miRNA expression analysis of archived patient material, consecutive cases of *H. pylori*-positive gastritis, of *H. pylori*-positive gastric low grade MALT lymphoma, and of gastric high grade MALT lymphoma were drawn from the surgical pathology files of the Institute of Pathology at the Cantonal Hospital St. Gallen, Switzerland. All data were blinded to guarantee patients' protection. All procedures were in agreement with the guidelines for use of human material in research issued by the participating Institutions' Ethics Committees.

RNA Extraction and Locked Nucleic Acid Real Time PCR for microRNA Quantification Total RNA was extracted from three 20 μm slices per sample of formalin fixed, paraffin embedded material using the RecoverAll total RNA Isolation kit (Ambion, Streetsville, Canada). Total RNA concentrations were measured using an ND-1000 spectrophotometer (NanoDrop Technologies). RNA integrity was confirmed on an Agilent 2100 Bioanalyzer (Agilent Technologies, Santa Clara, Calif., USA). The expression of mature miRNAs was analysed using the miR-CURY locked nucleic acid (LNA) microRNA PCR system following the manufacturer's instructions (Exiqon, Vedbaek, Denmark). 10 ng of total RNA was subjected to cDNA synthesis using either miRNA- or U6 snRNA-specific primers. The cDNA template was diluted 1:10 and real time PCR reactions were performed following the manufactures' recommendations (LightCycler; Roche, Basel, CH). Calculations of miRNA expression levels were performed using the comparative $\Delta\Delta C_t$ method and normalized against U6 snRNA levels.

Immunohistochemical Staining and Western Blotting

The gastric lymphoma tissue microarray used in this study was constructed as described (Bernasconi B. et al., Hum Pathol 2008, 39:536-42) and included a total of 76 specimens, comprising 39 cases of gastric low grade MALT lymphomas and 37 cases of gastric DLBCL. The following primary antibodies were used: anti-MYC (N-262; Santa Cruz Biotechnology, Santa Cruz, Calif., USA) and anti-FOXP1 (ICI2; Abcam, Cambridge, Mass., USA). MYC and FOXP1 levels were assessed by counting the number of positively staining tumour cells and graded using the following expression scale: a negligible level of staining of 0-10% was recorded as negative, while low expression was between 10-60% and high expression was recorded when 60-100% tumour cells stained positive. Protein extracts were made using 2× Laemmli sample buffer (4% SDS, 20% glycerol, 120 mM Tris pH 6.8).

Proteins were separated by SDS/polyacrylamide gel electrophoresis and transferred onto nitrocellulose membranes. Membranes were probed with antibodies against FOXP1 (JC12; Abcam) or against α-tubulin (Santa Cruz Biotechnology) to control for equivalent gel loading.

Cell Lines, Transfections and Luciferase Reporter Assays

On-target plus smartpool siRNAs for MYC, FOXP1 and a scrambled negative control was purchased from Dharmacon (Thermo Scientific, Lafayette, Colo., USA). Precursor microRNA oligonucleotides (pre-miR-let-7a, pre-miR-34a, pre-miR-23a, pre-miR-26a, pre-miR-150 and pre-miR-15) and scrambled negative control oligonucleotides were purchased from Ambion. For the purpose of siRNA or miRNA introduction into DLBCL cells, $1 \times 10^6$ cells were nucleoporated using an Amaxa Nucleoporator (Gaithersburg, Md., USA) with the specified amount of pre-miR miRNA precursor or siRNA. After 48 h, cells were harvested for RNA and protein analysis. After 72 h, tumor cell proliferation was quantified by [$^3$H]-thymidine incorporation assay as previously described (Craig V. J. et al., Blood 2010, 115:581-91). The pmirGLO Dual-Luciferase miRNA Target Expression Vector was purchased from Promega (Madison, Wis., USA). HEK293T cells were seeded into 21-well plates at $1 \times 10^5$ cells/well 24 h before transfection. 1 μg reporter plasmid containing the FOXP1 3'UTR or its mutants and 30 nM mir-34a precursor molecules were contransfected into each well using the Fugene 6 transfection reagent (Roche) in triplicates. Luciferase assays were performed 24 h after transfection using the Dual-Luciferase Reporter Assay System (Promega) with a Spectramax M5 reader (Molecular Devices, Sunnyvale, Calif., USA).

The invention claimed is:

1. A method of treating a B-cell lymphoma, the method comprising administering to a patient a therapeutically effective amount of a microRNA, wherein the B cell lymphoma is diffuse large B-cell lymphoma and wherein the microRNA is a member of the miR-34 family.

2. The method of claim 1, wherein the gastric B-cell lymphoma is high-grade gastric diffuse large B-cell lymphoma.

3. The method of claim 1, wherein the microRNA is miR-34a, miR-34b, miR-34c-5p or miR-34c-3p.

4. The method of claim 1, further comprising administering another active ingredient selected from cyclophosphamide, hydroxydaunorubicin, vincristine, prednisone/prednisolone, rituximab, or combinations thereof.

5. A method of treating gastric B-cell lymphoma or diffuse large B-cell lymphoma, the method comprising administering a therapeutically effective amount of a microRNA which is a member of the miR-34 family.

6. The method of claim 5, wherein the microRNA is miR-34a.

7. A method of treating a diffuse large B-cell lymphoma, comprising administering a therapeutically effective amount of a microRNA, wherein the diffuse large B-cell lymphoma is characterized by an over-expression of FoxP1, and wherein the microRNA is a member of the miR-34 family.

8. The method of claim 7, wherein the B-cell lymphoma is diffuse large B-cell lymphoma.

9. The method of claim 7, wherein the B-cell lymphoma is gastric B-cell lymphoma.

10. The method of claim 7, wherein the microRNA is miR-34a, miR-34b, miR-34c-5p or miR-34c-3p.

11. The method of claim 7, further comprising administering another active ingredient selected from cyclophosphamide, hydroxydaunorubicin, vincristine, prednisone/prednisolone, rituximab, or combinations thereof.

12. A method of treating gastric B-cell lymphoma or diffuse large B-cell lymphoma, the method comprising administering a therapeutically effective amount of a microRNA which is a member of the miR-34 family.

13. The method of claim 12, wherein the microRNA is miR-34a.

14. The method of claim 7, wherein the microRNA is miR-34a and the B-cell lymphoma is diffuse large B-cell lymphoma.

15. The method of claim 12, wherein the microRNA is miR-34a and the B-cell lymphoma is diffuse large B-cell lymphoma.

16. The method of claim 1, wherein the microRNA is miR-34a.

17. The method of claim 7, wherein the microRNA is miR-34a.

18. The method of claim 1, wherein the diffuse large B-cell lymphoma is gastric diffuse large B-cell lymphoma.

19. The method of claim 5, wherein the diffuse large B-cell lymphoma is gastric diffuse large B-cell lymphoma.

* * * * *

```
                        SEQUENCE LISTING

<160> NUMBER OF SEQ ID NOS: 9

<210> SEQ ID NO 1
<211> LENGTH: 22
<212> TYPE: RNA
<213> ORGANISM: Homo sapiens

<400> SEQUENCE: 1
uggcaguguc uuagcugguu gu                                                22

<210> SEQ ID NO 2
<211> LENGTH: 22
<212> TYPE: RNA
<213> ORGANISM: Homo sapiens

<400> SEQUENCE: 2
caaucacuaa cuccacugcc au                                                22

<210> SEQ ID NO 3
<211> LENGTH: 23
<212> TYPE: RNA
<213> ORGANISM: Homo sapiens

<400> SEQUENCE: 3
aggcagugua guuagcugau ugc                                               23

<210> SEQ ID NO 4
<211> LENGTH: 22
<212> TYPE: RNA
<213> ORGANISM: Homo sapiens

<400> SEQUENCE: 4
aaucacuaac cacacggcca gg                                                22

<210> SEQ ID NO 5
<211> LENGTH: 22
<212> TYPE: RNA
<213> ORGANISM: Homo sapiens

<400> SEQUENCE: 5
uagcagcaca uaaugguuug ug                                                22

<210> SEQ ID NO 6
<211> LENGTH: 21
<212> TYPE: RNA
<213> ORGANISM: Homo sapiens
```

```
<400> SEQUENCE: 6
aucacauugc cagggauuuc c                                              21

<210> SEQ ID NO 7
<211> LENGTH: 22
<212> TYPE: RNA
<213> ORGANISM: Homo sapiens

<400> SEQUENCE: 7
uucaaguaau ccaggauagg cu                                             22

<210> SEQ ID NO 8
<211> LENGTH: 22
<212> TYPE: RNA
<213> ORGANISM: Homo sapiens

<400> SEQUENCE: 8
ucucccaacc cuuguaccag ug                                             22

<210> SEQ ID NO 9
<211> LENGTH: 22
<212> TYPE: RNA
<213> ORGANISM: Homo sapiens

<400> SEQUENCE: 9
ugagguagua gguuguauag uu                                             22
```